(12) United States Patent
Knapp et al.

(10) Patent No.: US 11,490,983 B2
(45) Date of Patent: Nov. 8, 2022

(54) CATHETERIZATION PACKAGES AND METHODS THEREOF

(71) Applicant: C. R. Bard, Inc., Franklin Lakes, NJ (US)

(72) Inventors: Tracey E. Knapp, Snellville, GA (US); Eric Rehm, Lawrenceville, GA (US); Nick Austerman, Atlanta, GA (US); Sarah Skelton, Atlanta, GA (US); Caroline Bunn, Atlanta, GA (US); Robert M. Hine, Covington, GA (US); Brandt Davis, Milford, OH (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 98 days.

(21) Appl. No.: 16/639,059

(22) PCT Filed: Apr. 23, 2019

(86) PCT No.: PCT/US2019/028784
§ 371 (c)(1),
(2) Date: Feb. 13, 2020

(87) PCT Pub. No.: WO2019/209867
PCT Pub. Date: Oct. 31, 2019

(65) Prior Publication Data
US 2020/0360103 A1 Nov. 19, 2020

Related U.S. Application Data

(60) Provisional application No. 62/662,095, filed on Apr. 24, 2018.

(51) Int. Cl.
*A61B 50/33* (2016.01)
*A61M 25/00* (2006.01)
(Continued)

(52) U.S. Cl.
CPC .......... *A61B 50/33* (2016.02); *A61M 25/002* (2013.01); *B29D 22/003* (2013.01); *B65B 5/02* (2013.01);
(Continued)

(58) Field of Classification Search
CPC ... A61B 50/33; A61B 50/30; A61B 2050/005; A61B 2050/3008; B65D 77/20; A61M 25/002
(Continued)

(56) References Cited

U.S. PATENT DOCUMENTS 935,419 A    9/1909  Smith
2,346,636 A  4/1944  Porter
(Continued)

FOREIGN PATENT DOCUMENTS

CN    1511014 A    7/2004
CN    201823147 U  5/2011
(Continued)

OTHER PUBLICATIONS

PCT/US20/35371 filed May 29, 2020 International Search Report and Written Opinion dated Sep. 14, 2020.
(Continued)

*Primary Examiner* — Steven A. Reynolds
(74) *Attorney, Agent, or Firm* — Rutan & Tucker LLP

(57) ABSTRACT

Disclosed is a catheterization package including catheterization-package components and a catheterization tray configured to facilitate a catheterization procedure. The catheterization-package components include a urinary catheter fluidly connected to a urine-drainage bag and a sampling-port access device configured to fluidly connect to a urine-sampling port of the urinary catheter or the urine-drainage bag for aseptic collection of one or more urine samples. The catheterization tray includes at least a first compartment, a
(Continued)

second compartment, and a third compartment configured to hold the catheterization-package components. The first compartment is configured to hold the urinary catheter. The second compartment is connected to the first compartment by an intercompartment connection. The second compartment is configured to hold the urine-drainage bag. The third compartment is configured to hold the sampling-port access device. Step-by-step instructions are incorporated into the catheterization tray to facilitate the catheterization procedure. Also disclosed are methods for the catheterization package.

20 Claims, 8 Drawing Sheets

(51) Int. Cl.
| | |
|---|---|
| B29D 22/00 | (2006.01) |
| B65B 5/02 | (2006.01) |
| B65B 5/08 | (2006.01) |
| B65D 77/20 | (2006.01) |
| A61B 50/00 | (2016.01) |
| A61B 50/30 | (2016.01) |

(52) U.S. Cl.
CPC ............. B65B 5/08 (2013.01); B65D 77/20 (2013.01); *A61B 2050/005* (2016.02); *A61B 2050/3008* (2016.02)

(58) Field of Classification Search
USPC ........................................................ 206/571
See application file for complete search history.

(56) References Cited

U.S. PATENT DOCUMENTS

| | | | |
|---|---|---|---|
| 2,659,485 A | 11/1953 | Duley et al. |
| 2,874,707 A | 2/1959 | Koppel |
| 2,947,415 A | 8/1960 | Garth |
| 3,107,786 A | 10/1963 | Adelman |
| 3,137,387 A | 6/1964 | Overment |
| 3,138,253 A | 6/1964 | Harautuneian |
| 3,144,932 A | 8/1964 | Zerbo, Jr. |
| 3,166,189 A | 1/1965 | Disston |
| 3,324,855 A | 6/1967 | Heimlich |
| 3,329,261 A | 7/1967 | Serany, Jr. et al. |
| 3,345,988 A | 10/1967 | Vitello |
| 3,379,339 A | 4/1968 | Asenbauer |
| 3,485,352 A | 12/1969 | Pilger |
| D218,077 S | 7/1970 | Gabriel |
| 3,542,019 A | 11/1970 | Gittins |
| D222,312 S | 10/1971 | Kurtz et al. |
| 3,642,123 A | 2/1972 | Knox |
| 3,650,393 A | 3/1972 | Reiss et al. |
| 3,726,281 A | 4/1973 | Norton et al. |
| 3,762,399 A | 10/1973 | Riedell |
| 3,770,119 A | 11/1973 | Hultberg et al. |
| 3,802,555 A | 4/1974 | Grasty et al. |
| 3,851,649 A | 12/1974 | Villari |
| D234,404 S | 2/1975 | Merril |
| 3,901,235 A | 8/1975 | Patel et al. |
| D237,315 S | 10/1975 | Nowakowski |
| D237,317 S | 10/1975 | Nowakowski |
| 3,965,900 A | 6/1976 | Boedecker |
| 3,967,728 A | 7/1976 | Gordon et al. |
| 3,976,195 A | 8/1976 | Cohen |
| 3,978,983 A | 9/1976 | Brezette |
| 3,981,398 A | 9/1976 | Boshoff |
| D242,654 S | 12/1976 | Rawls |
| 3,998,221 A | 12/1976 | Collins |
| D243,798 S | 3/1977 | Swartz |
| 4,011,944 A | 3/1977 | Cooley et al. |
| 4,053,280 A | 10/1977 | Salisbury |
| 4,085,845 A | 4/1978 | Perfect |
| D248,871 S | 8/1978 | Forsman et al. |
| D249,362 S | 9/1978 | Forsman et al. |
| 4,140,127 A | 2/1979 | Cianci et al. |
| 4,149,635 A | 4/1979 | Stevens |
| 4,153,160 A | 5/1979 | Leigh |
| 4,160,505 A | 7/1979 | Rauschenberger |
| 4,170,300 A | 10/1979 | Pick |
| 4,226,328 A | 10/1980 | Beddow |
| 4,256,225 A | 3/1981 | Jackson |
| 4,262,800 A | 4/1981 | Nethercutt |
| 4,266,669 A | 5/1981 | Watson |
| D262,995 S | 2/1982 | Gaba et al. |
| 4,332,322 A | 6/1982 | Jaeschke et al. |
| 4,334,537 A | 6/1982 | Peterson |
| 4,366,901 A | 1/1983 | Short |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,501,363 A | 2/1985 | Isbey, Jr. |
| 4,522,302 A | 6/1985 | Paikoff |
| 4,523,679 A | 6/1985 | Paikoff et al. |
| 4,530,349 A | 7/1985 | Metzger |
| D280,663 S | 9/1985 | Albon et al. |
| D280,933 S | 10/1985 | McLaughlin |
| D283,051 S | 3/1986 | Fichera |
| 4,595,102 A | 6/1986 | Cianci et al. |
| D287,760 S | 1/1987 | Discko, Jr. |
| 4,767,008 A | 8/1988 | Warnecke et al. |
| 4,795,441 A | 1/1989 | Bhatt |
| 4,811,847 A | 3/1989 | Reif et al. |
| 4,828,113 A | 5/1989 | Friedland et al. |
| 4,844,259 A | 7/1989 | Glowczewskie, Jr. et al. |
| 4,858,821 A | 8/1989 | Bickelhaupt |
| 4,925,448 A | 5/1990 | Bazaral |
| 4,928,830 A | 5/1990 | Brewer |
| 4,944,427 A | 7/1990 | Yamada et al. |
| D310,896 S | 9/1990 | Winjum |
| 4,989,733 A | 2/1991 | Patry |
| 5,007,535 A | 4/1991 | Meseke et al. |
| 5,024,326 A | 6/1991 | Sandel et al. |
| 5,031,768 A | 7/1991 | Fischer |
| 5,098,391 A | 3/1992 | Pantages et al. |
| 5,163,557 A | 11/1992 | Sokolowski |
| 5,170,804 A | 12/1992 | Glassman |
| 5,174,306 A | 12/1992 | Marshall |
| D334,973 S | 4/1993 | Valentine et al. |
| D337,830 S | 7/1993 | Coyne et al. |
| 5,242,398 A | 9/1993 | Knoll et al. |
| D343,687 S | 1/1994 | Houghton et al. |
| 5,306,239 A | 4/1994 | Gurmarnik et al. |
| 5,318,543 A | 6/1994 | Ross et al. |
| 5,322,163 A | 6/1994 | Foos |
| 5,339,955 A | 8/1994 | Horan et al. |
| D351,661 S | 10/1994 | Fischer |
| D353,078 S | 12/1994 | Davis et al. |
| 5,384,103 A | 1/1995 | Miller |
| 5,392,918 A | 2/1995 | Harrison |
| 5,394,983 A | 3/1995 | Latulippe et al. |
| 5,449,071 A | 9/1995 | Levy |
| 5,525,314 A | 6/1996 | Hurson |
| 5,586,163 A | 12/1996 | Goldstein |
| 5,590,778 A | 1/1997 | Dutchik |
| D380,272 S | 6/1997 | Partika et al. |
| D387,177 S | 12/1997 | Davis |
| D387,559 S | 12/1997 | Williamson |
| 5,704,914 A | 1/1998 | Stocking et al. |
| 5,752,234 A | 5/1998 | Withers |
| 5,779,053 A | 7/1998 | Partika et al. |
| 5,810,738 A | 9/1998 | Thomas, II |
| 5,931,303 A | 8/1999 | Salvadori |
| 5,941,241 A | 8/1999 | Weinstein et al. |
| 5,947,284 A | 9/1999 | Foster |
| 5,947,890 A | 9/1999 | Spencer et al. |
| 5,975,295 A | 11/1999 | Diamond |
| 6,004,136 A | 12/1999 | Ehrenpreis |
| 6,012,586 A | 1/2000 | Misra |

(56) References Cited

U.S. PATENT DOCUMENTS

| | | |
|---|---|---|
| 6,068,121 A | 5/2000 | McGlinch |
| 6,090,075 A | 7/2000 | House |
| 6,142,152 A | 11/2000 | Gawarecki |
| 6,158,437 A | 12/2000 | Vagley |
| D437,941 S | 2/2001 | Frattini |
| D442,697 S | 5/2001 | Hajianpour |
| D445,198 S | 7/2001 | Frattini |
| D450,130 S | 11/2001 | Goldstein |
| D450,391 S | 11/2001 | Hunt et al. |
| 6,382,212 B1 | 5/2002 | Borchard |
| 6,405,863 B1 | 6/2002 | Dhindsa |
| 6,412,639 B1 | 7/2002 | Hickey |
| 6,454,097 B1 | 9/2002 | Blanco |
| 6,502,699 B1 | 1/2003 | Watson |
| D471,640 S | 3/2003 | McMichael et al. |
| D471,641 S | 3/2003 | McMichael et al. |
| 6,579,271 B1 | 6/2003 | Aruffo et al. |
| D480,816 S | 10/2003 | McMichael et al. |
| 6,640,976 B1 | 11/2003 | Franks-Farah et al. |
| 6,681,933 B1 | 1/2004 | Demsien et al. |
| 6,769,546 B2 | 8/2004 | Busch |
| D495,491 S | 9/2004 | Ramirez et al. |
| D495,807 S | 9/2004 | Agbodoe et al. |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,907,992 B2 | 6/2005 | McMichael et al. |
| 6,910,581 B2 | 6/2005 | McMichael et al. |
| 6,915,901 B2 | 7/2005 | Feinberg et al. |
| 6,926,708 B1 | 8/2005 | Franks-Farah et al. |
| 6,948,742 B2 | 9/2005 | Buck |
| 6,959,808 B2 | 11/2005 | Discko, Jr. |
| 6,991,096 B2 | 1/2006 | Gottlieb et al. |
| 7,048,120 B2 | 5/2006 | Pond |
| 7,066,328 B2 | 6/2006 | Pulsifer |
| D530,920 S | 10/2006 | Snell |
| D547,064 S | 7/2007 | Snell |
| D549,454 S | 8/2007 | Åhman |
| 7,264,869 B2 | 9/2007 | Tobita et al. |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 | 7/2008 | McMichael et al. |
| 7,410,053 B2 | 8/2008 | Bowen et al. |
| 7,434,687 B2 | 10/2008 | Itou et al. |
| D579,662 S | 11/2008 | Dretzka |
| 7,491,176 B2 | 2/2009 | Mann |
| 7,494,487 B2 | 2/2009 | Timm |
| D590,596 S | 4/2009 | Dretzka |
| D596,311 S | 7/2009 | Antons |
| 7,624,869 B2 | 12/2009 | Primer |
| 7,634,893 B2 | 12/2009 | Gottlieb et al. |
| D609,819 S | 2/2010 | Tomes et al. |
| 7,662,146 B2 | 2/2010 | House |
| D612,153 S | 3/2010 | Liao |
| 7,671,014 B2 | 3/2010 | Beals et al. |
| D613,418 S | 4/2010 | Ryan et al. |
| D618,821 S | 6/2010 | Larsen |
| 7,743,918 B2 | 6/2010 | Itou et al. |
| 7,785,312 B2 | 8/2010 | Thorne, Jr. et al. |
| D623,765 S | 9/2010 | Tomes et al. |
| D631,558 S | 1/2011 | Harmston et al. |
| D636,894 S | 4/2011 | Tomes et al. |
| D638,137 S | 5/2011 | Gross et al. |
| 7,993,326 B2 | 8/2011 | Massengale et al. |
| D646,796 S | 10/2011 | Walter |
| D650,912 S | 12/2011 | Tomes et al. |
| 8,128,595 B2 | 3/2012 | Walker et al. |
| 8,177,064 B2 | 5/2012 | McCormick et al. |
| D662,218 S | 6/2012 | Pittman |
| 8,240,468 B2 | 8/2012 | Wilkinson et al. |
| 8,273,312 B2 * | 9/2012 | Porat .................. B01L 3/502 435/31 |
| 8,282,829 B2 | 10/2012 | Yu et al. |
| 8,448,786 B2 | 5/2013 | Tomes et al. |
| D688,461 S | 8/2013 | Ambrefe, Jr. et al. |
| 8,584,849 B2 | 11/2013 | McCaffrey |
| 8,597,505 B2 | 12/2013 | Fulkerson et al. |
| 8,628,549 B2 | 1/2014 | To et al. |
| 8,631,935 B2 | 1/2014 | Tomes et al. |
| 8,656,929 B2 | 2/2014 | Miller et al. |
| 8,662,306 B2 | 3/2014 | Agrawal |
| 8,678,190 B2 | 3/2014 | Tomes et al. |
| 8,708,999 B2 | 4/2014 | Hong et al. |
| D704,856 S | 5/2014 | Tomes et al. |
| D707,848 S | 6/2014 | Shigeno et al. |
| 8,746,452 B2 | 6/2014 | Tomes et al. |
| D708,347 S | 7/2014 | Lober |
| D708,759 S | 7/2014 | Heyman et al. |
| 8,875,940 B2 | 11/2014 | Danchisin et al. |
| D720,470 S | 12/2014 | Lober |
| D720,471 S | 12/2014 | Angel et al. |
| 9,084,593 B2 | 7/2015 | Yakel et al. |
| D738,491 S | 9/2015 | Foley et al. |
| 9,162,781 B2 | 10/2015 | Lien |
| 9,186,217 B2 | 11/2015 | Goyal |
| D751,726 S | 3/2016 | Nishioka et al. |
| 9,283,352 B2 | 3/2016 | Tomes et al. |
| 9,486,604 B2 | 11/2016 | Murray et al. |
| 9,522,001 B2 | 12/2016 | Bui et al. |
| 9,522,753 B2 | 12/2016 | Tomes et al. |
| 9,693,756 B2 | 7/2017 | Tomes et al. |
| 9,744,333 B2 | 8/2017 | Terzibashian |
| 9,745,088 B2 | 8/2017 | Tomes et al. |
| 9,795,761 B2 | 10/2017 | Lockwood et al. |
| 9,808,400 B2 | 11/2017 | Tomes et al. |
| 9,808,596 B2 | 11/2017 | Tomes et al. |
| 9,872,969 B2 | 1/2018 | Conway et al. |
| 10,022,464 B2 | 7/2018 | Sarphati et al. |
| 10,039,897 B2 | 8/2018 | Norris et al. |
| 10,106,295 B2 | 10/2018 | Lockwood |
| 10,251,812 B2 | 4/2019 | Tomes et al. |
| 10,512,752 B2 | 12/2019 | Tomes et al. |
| 10,639,120 B2 | 5/2020 | Turturro et al. |
| 2002/0185406 A1 | 12/2002 | Massengale et al. |
| 2003/0038475 A1 | 2/2003 | Stancil |
| 2003/0060761 A1 | 3/2003 | Evans et al. |
| 2003/0075474 A1 | 4/2003 | Moyer et al. |
| 2003/0159966 A1 | 8/2003 | McMichael et al. |
| 2003/0159967 A1 | 8/2003 | McMichael et al. |
| 2003/0159968 A1 | 8/2003 | McMichael et al. |
| 2003/0159969 A1 | 8/2003 | McMichael et al. |
| 2003/0211627 A1 | 11/2003 | Koesterman et al. |
| 2004/0004019 A1 | 1/2004 | Busch |
| 2004/0055919 A1 | 3/2004 | Rowe et al. |
| 2004/0060260 A1 | 4/2004 | Gottlieb et al. |
| 2004/0111072 A1 | 6/2004 | McKissick |
| 2004/0161732 A1 | 8/2004 | Stump et al. |
| 2004/0180822 A1 | 9/2004 | Grafton |
| 2004/0195145 A1 | 10/2004 | Roshdy |
| 2004/0200754 A1 | 10/2004 | Hagemeier |
| 2004/0238391 A1 | 12/2004 | Pond |
| 2005/0022822 A1 | 2/2005 | Santilli et al. |
| 2005/0098470 A1 | 5/2005 | Davis et al. |
| 2005/0101905 A1 | 5/2005 | Merry |
| 2005/0236940 A1 | 10/2005 | Rockoff |
| 2005/0256453 A1 | 11/2005 | Nagamatsu |
| 2005/0285385 A1 | 12/2005 | Bova et al. |
| 2006/0009742 A1 | 1/2006 | Solazzo |
| 2006/0086634 A1 | 4/2006 | Steppe |
| 2006/0104857 A1 | 5/2006 | Pigott et al. |
| 2006/0186010 A1 | 8/2006 | Warnack et al. |
| 2006/0205996 A1 | 9/2006 | Presthus et al. |
| 2006/0264822 A1 | 11/2006 | Nagamatsu |
| 2006/0271019 A1 | 11/2006 | Stoller et al. |
| 2006/0282045 A1 | 12/2006 | Wilkinson et al. |
| 2007/0026472 A1 | 2/2007 | Prokash et al. |
| 2007/0049806 A1 | 3/2007 | Adams et al. |
| 2007/0060908 A1 | 3/2007 | Webster et al. |
| 2007/0084742 A1 | 4/2007 | Miller et al. |
| 2007/0088330 A1 | 4/2007 | House |
| 2007/0095699 A1 | 5/2007 | Frieze et al. |
| 2007/0142786 A1 | 6/2007 | Lampropoulos et al. |

(56) References Cited

U.S. PATENT DOCUMENTS

| | | |
|---|---|---|
| 2007/0156099 A1 | 7/2007 | Fowler |
| 2007/0161971 A1 | 7/2007 | House |
| 2007/0197998 A1 | 8/2007 | Itou et al. |
| 2007/0225687 A1 | 9/2007 | House |
| 2007/0273258 A1 | 11/2007 | Ernst |
| 2007/0299431 A1 | 12/2007 | Jakubowski et al. |
| 2008/0045861 A1 | 2/2008 | Miller et al. |
| 2008/0058725 A1 | 3/2008 | Scribner et al. |
| 2008/0116106 A1 | 5/2008 | Lampropoulos et al. |
| 2008/0121553 A1 | 5/2008 | Gobel |
| 2008/0125722 A1 | 5/2008 | Hess et al. |
| 2008/0172042 A1 | 7/2008 | House |
| 2008/0221515 A1 | 9/2008 | Nagamatsu |
| 2008/0249482 A1 | 10/2008 | Erez |
| 2008/0272023 A1 | 11/2008 | McCormick et al. |
| 2008/0283426 A1 | 11/2008 | Primer et al. |
| 2008/0283433 A1 | 11/2008 | Primer |
| 2009/0026146 A1 | 1/2009 | Carlisle et al. |
| 2009/0076461 A1 | 3/2009 | Susi et al. |
| 2009/0184026 A1 | 7/2009 | Massengale et al. |
| 2009/0194453 A1 | 8/2009 | Thorne, Jr. et al. |
| 2009/0208368 A1 | 8/2009 | Waldrep et al. |
| 2009/0234346 A1 | 9/2009 | McBride, Jr. et al. |
| 2009/0236259 A1 | 9/2009 | Hicks |
| 2010/0274205 A1 | 10/2010 | Morelli et al. |
| 2010/0307941 A1 | 12/2010 | Tomes et al. |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0120906 A1 | 5/2011 | Umholtz et al. |
| 2011/0155599 A1 | 6/2011 | Yakel et al. |
| 2011/0203957 A1 | 8/2011 | Zoland et al. |
| 2011/0232234 A1 | 9/2011 | Lockwood et al. |
| 2011/0233079 A1 | 9/2011 | Macinnes et al. |
| 2011/0284410 A1 | 11/2011 | Lockwood |
| 2011/0290260 A1 | 12/2011 | Tomes et al. |
| 2011/0290262 A1 | 12/2011 | Tomes et al. |
| 2011/0297147 A1 | 12/2011 | Lick et al. |
| 2012/0145589 A1 | 6/2012 | MacInnes et al. |
| 2012/0150123 A1 | 6/2012 | Lawrence et al. |
| 2012/0222686 A1 | 9/2012 | Lockwood et al. |
| 2012/0271161 A1 | 10/2012 | Buckberry |
| 2012/0298114 A1 | 11/2012 | Landsman et al. |
| 2013/0037440 A1 | 2/2013 | Danchisin et al. |
| 2013/0042576 A1 | 2/2013 | Sweeney |
| 2013/0245496 A1 | 9/2013 | Wells et al. |
| 2013/0269713 A1 | 10/2013 | Bui et al. |
| 2013/0277248 A1 | 10/2013 | Tomes et al. |
| 2013/0277262 A1 | 10/2013 | Nemard |
| 2014/0021087 A1 | 1/2014 | Adler et al. |
| 2014/0039349 A1 | 2/2014 | Moghe et al. |
| 2014/0100551 A1 | 4/2014 | Holmstrom |
| 2014/0142465 A1 | 5/2014 | Tomes et al. |
| 2014/0231287 A1 | 8/2014 | Tomes et al. |
| 2014/0231288 A1 | 8/2014 | Tomes et al. |
| 2014/0262851 A1 | 9/2014 | Adler et al. |
| 2015/0048103 A1 | 2/2015 | Danchisin et al. |
| 2015/0083627 A1 | 3/2015 | Gorman |
| 2015/0151017 A1 | 6/2015 | Tipton et al. |
| 2015/0258304 A1 | 9/2015 | Tomes et al. |
| 2015/0283354 A1 | 10/2015 | Olson et al. |
| 2015/0335855 A1 | 11/2015 | Tomes et al. |
| 2016/0166800 A1 | 6/2016 | Tomes et al. |
| 2016/0193444 A1 | 7/2016 | Tomes et al. |
| 2016/0228676 A1* | 8/2016 | Glithero ................ A61B 90/94 |
| 2016/0243332 A1 | 8/2016 | Portela et al. |
| 2017/0056122 A1 | 3/2017 | Ramsey |
| 2017/0056125 A1 | 3/2017 | Garza et al. |
| 2017/0086746 A1 | 3/2017 | Ofek et al. |
| 2017/0106165 A1 | 4/2017 | Holmes |
| 2017/0202699 A1 | 7/2017 | Zani et al. |
| 2017/0216557 A1 | 8/2017 | Kearns et al. |
| 2017/0216558 A1 | 8/2017 | Hughett et al. |
| 2017/0231804 A1 | 8/2017 | Miller et al. |
| 2017/0232226 A1 | 8/2017 | Loui et al. |
| 2017/0296282 A1 | 10/2017 | Turturro et al. |
| 2017/0296283 A1 | 10/2017 | Turturro et al. |
| 2017/0296284 A1 | 10/2017 | Turturro et al. |
| 2017/0319183 A1 | 11/2017 | Tomes et al. |
| 2017/0349305 A1 | 12/2017 | Tomes et al. |
| 2017/0368302 A1 | 12/2017 | Brooks et al. |
| 2018/0001052 A1 | 1/2018 | Lockwood et al. |
| 2018/0056030 A1* | 3/2018 | Tomes ................ A61B 50/33 |
| 2018/0057196 A1 | 3/2018 | Tomes et al. |
| 2018/0206933 A1 | 7/2018 | Healey et al. |
| 2018/0221564 A1 | 8/2018 | Patel et al. |
| 2019/0151195 A1 | 5/2019 | Tomes et al. |
| 2020/0353204 A1 | 11/2020 | Glithero et al. |
| 2021/0100978 A1 | 4/2021 | Gohde |

FOREIGN PATENT DOCUMENTS

| | | |
|---|---|---|
| DE | 102007003223 B4 | 12/2009 |
| EP | 1301782 A1 | 4/2003 |
| EP | 1595561 A2 | 11/2005 |
| EP | 1731189 A1 | 12/2006 |
| FR | 2780274 A1 | 12/1999 |
| FR | 2873929 A1 | 2/2006 |
| GB | 2365342 A | 2/2002 |
| JP | S50-149175 A | 11/1975 |
| JP | 2002-136597 A | 5/2002 |
| JP | 2005-506110 A | 3/2005 |
| JP | 2007-229520 A | 9/2007 |
| JP | 2007-319535 A | 12/2007 |
| JP | 2010-200809 A | 9/2010 |
| JP | 2011-520578 A | 7/2011 |
| WO | 9106255 A1 | 5/1991 |
| WO | 9607364 A1 | 3/1996 |
| WO | 02/004942 A1 | 1/2002 |
| WO | 02064078 A1 | 8/2002 |
| WO | 2002083021 A1 | 10/2002 |
| WO | 2004005157 A1 | 1/2004 |
| WO | 2005/027767 A1 | 3/2005 |
| WO | 2006114466 A1 | 11/2006 |
| WO | 2007/045943 A1 | 4/2007 |
| WO | 08033873 A2 | 3/2008 |
| WO | 2008139852 A1 | 11/2008 |
| WO | 2015057999 | 4/2015 |
| WO | 2017147067 A1 | 8/2017 |
| WO | 2018044772 A1 | 3/2018 |
| WO | 2018057835 A1 | 3/2018 |
| WO | 2018/183752 A1 | 10/2018 |
| WO | 2018/190865 A1 | 10/2018 |
| WO | 2019/209867 A1 | 10/2019 |
| WO | 2021/081434 A1 | 4/2021 |

OTHER PUBLICATIONS

U.S. Appl. No. 15/487,297, filed Apr. 13, 2017 Notice of Allowance dated Oct. 2, 2020.
U.S. Appl. No. 15/487,297, filed Apr. 13, 2017 Restriction Requirement dated Jun. 11, 2020.
"Arrow International, Inc. Introduces Maximal Barrier Precautions Tray", Press release. Jan. 11, 2006.
"Uniting the best of Healthcare" http://ghx.com/about/, last accessed 2019.
Addison, R et al., "Catheter Care," Royal College of Nursing, London (2008).
American Journal of Infection Control. Vol. 46 (2018) SI6-67.
Arrow, "Arrow Trauma Products" brochure, 2000.
AU 2014337176 filed Mar. 15, 2016 Examination Report dated Aug. 1, 2018.
Bardex LC. Complete Care StateLock Device 350 ml Urine Meter Foley Tray with Bacteriostatic Collection System, Directions for Use; Dated 2006.
Bardex LC. Infection Control 350 ml Urine Meter Foley Tray, Directions for Use; Dated 2006.
Bardex LC. Infection Control Foley Tray, Directions for Use; Dated 2006.
C. R. Bard Urological Drainage, https://www.crbard.com/medical/Professionals/Product-Concentrations/Urological-Drainage, last accessed 2019.

(56) References Cited

OTHER PUBLICATIONS

C.R. Bard, Inc; "A few important words about Catheter Care"; Dated 2001.
California Department of Public Health, "Catheter-Associated Urinary Tract Infection (CAUTI) Prevention" (2015).
CN 201480057141.5 filed Apr. 18, 2016 Office Action dated Dec. 4, 2018.
Dept. of Health and Human Services, "Action Plan to Prevent Healthcare-Associated Infections." (2009).
Dobkin et al., "Myth and Measurement—The Case of Medical Bankruptcies," 378 New Eng. J. Med., 1076-78 (2018).
Ellen Elpern, et al., "Prevention of Catheter-Associated Urinary Tract Infections in Adults," 36 Critical Care Nurse, 9 (2016).
EP 14853869.7 filed Mar. 31, 2016 Extended European Search Report dated Aug. 4, 2017.
EP 14853869.7 filed Mar. 31, 2016 Office Action dated Mar. 13, 2019.
Foxman, B. "Epidemiology of Urinary Tract Infections: Incidence, Morbidity, and Economic Costs." The American Journal of Medicine, 113 Suppl 1A (2002).
Gould et al., "Catheter-associated Urinary Tract Infection (CAUTI) Toolkit," Centers for Disease Control and Prevention Devision of Healthcare Quality Promotion. (2009).
Gould et al., "Guideline for Prevention of Catheter Associated Urinary Tract Infections," Centers for Disease Control Healthcare Infection Control Practices Advisory Committee, (2009).
Greene, L. et al. "Guide to the Elimination of Catheter-Associated Urinary Tract infections (CAUTIs): Developing and Applying Facility-Based Prevention Interventions in Acute and Long-Term Care Settings," Association for Professionals in Infection Control and Epidemiology, (2008).
Jacobsen, S.M. et al., "Complicated Catheter-Associated Urinary Tract Infections Due to *Escherichia coli* and Proteus mirabilis", 21 Clinical Microbiology Reviews 1, 26-59 (Jan. 2008).
Jennifer A Meddings, "Implementing Strategies to Reduce Hospital-Acquired Catheter-Associated Urinary Tract Infection," Wound, Ostomy and Continence Nurses Society, www.catheterout.org, (Jun. 2010).
JP 2016-523921 filed Apr. 15, 2016 Office Action dated Jul. 11, 2018.
Linda Kohn et al., eds., "To Err is Human: Building a Safer Health System," Institute of Medicine (US), (2000).
Lo, E. et al., "Strategies to Prevent Catheter-Associated Urinary Tract Infections in Acute Care Hospitals," Infection Control and Hospital Epidemiology. 29, S41-S50 (2008).
Madeo M. et al., "Reducing the risks associated with urinary catheters." Nursing Standard, vol. 23, No. 29, 47-55 (2009).
Male Catheter Insertion Video, Uploaded to YouTube on Feb. 7, 2008, Parts 1 and 2. https://www.youtube.com/watch?v=ISBAya_5cIM (Last accessed Feb. 26, 2020).
Norman, Donald A., The Design of Everyday Things, 2002 ed. (Excerpt).
Ortega, R. et. al. "Female Urethral Catheterization", N Engl J Med 2008; 358: e15. Apr. 3, 2008.
PCT/US14/60963 filed Oct. 16, 2014 International Search Report and Written Opinion dated Jan. 14, 2015.
PCT/US2017/027628 filed Apr. 14, 2017 International Search Report and Written Opinion dated Jul. 17, 2017.
PCT/US2018/025260 filed Mar. 29, 2018 International Search Report and Written Opinion dated Jun. 7, 2018.
Request for Inter partes Review of U.S. Pat. No. 8,631,935, filed Dec. 30, 2014.
Saint et al., "Catheter-Associated Urinary Tract Infection and the Medicare Rule Changes," Annals of Internal Medicine, Jun. 16, 2009.
Steultjens, M.P.M. et al., "Range of joint motion and disability in patients with osteoarthritis of the knee or hip," Rheumatology, Bristish Society for Rheumatology. (2000).
The Joint Commision on National Patient Safety, "2012 National Patient Safety Goals: Hospital accreditation Program." (2012).
Thomson et al. "Male Urethral Catheterization", N Engl J Med 2006; 354: e22. May 25, 2006.
Urological Drainage website, http://rn.bardmedical.com/products/urological-drainage/, last accessed 2019.
U.S. Appl. No. 15/029,613, filed Apr. 14, 2016 Final Office Action dated Apr. 10, 2019.
U.S. Appl. No. 15/029,613, filed Apr. 14, 2016 Non-Final Office Action dated Nov. 29, 2018.
U.S. Appl. No. 15/487,297, filed Apr. 13, 2017 Advisory Action dated Apr. 28, 2020.
U.S. Appl. No. 15/487,297, filed Apr. 13, 2017 Final Office Action dated Feb. 21, 2020.
U.S. Appl. No. 15/487,297, filed Apr. 13, 2017 Non-Final Office Action dated Apr. 5, 2019.
U.S. Appl. No. 15/487,297, filed Apr. 13, 2017 Restriction Requirement dated Nov. 29, 2018.
Raheem, "Application of Plastics and Paper as Food Packaging Materials" An Overview, 2017, Emirates Journal of Food and Agriculture, vol. 25, pp. 177-188 (Year: 2017).
U.S. Appl. No. 16/497,770, filed Sep. 25, 2019 Non-Final Office Action dated Jun. 1, 2022.
U.S. Appl. No. 17/058,067, filed Nov. 23, 2020 Non-Final Office Action dated Jul. 7, 2022.

* cited by examiner

CATHETERIZATION PACKAGES AND METHODS THEREOF

PRIORITY

This application is a U.S. national stage application from International Application No. PCT/US2019/028784, filed Apr. 23, 2019, which claims the benefit of priority to U.S. Provisional Patent Application No. 62/662,095, filed Apr. 24, 2018, each of which is incorporated by reference in its entirety into this application.

BACKGROUND

Catheters suitable for draining a patient's bladder include indwelling catheters. Indwelling catheters include Foley catheters, which are typically indicated for surgical and medical patients that require, at least temporarily, assisted bladder voiding. Common indications include acute or chronic urinary retention, medical procedures that may at least temporarily limit a patient's movement, a need for accurate monitoring of fluid input and urine output such as in an intensive care unit ("ICU"), benign prostatic hyperplasia, incontinence, or the effects of various surgical interventions involving the bladder or the prostate.

A standard Foley catheter design includes a balloon disposed at the distal end of the catheter to anchor the catheter in the bladder. The catheter includes at least one lumen to drain urine from the bladder and at least one lumen to inflate the balloon (e.g., with sterile water). The proximal end of the Foley catheter includes at least two ports in communication with the two lumens, a first port that is connected to the drainage lumen and has an interface with fittings for drainage and sampling, and a second port that is connected to the inflation lumen with a valve to ensure the inflation fluid remains within the lumen and balloon once filled. A tip of the standard Foley catheter extends beyond the sides of the balloon into the bladder and includes one or more apertures or "eyes" to drain fluids and debris from the bladder. This standard design has not changed in approximately 100 years, although catheters with various additions (e.g., mechanical anchors, etc.) and improvements have been proposed and investigated.

Catheters suitable for draining a patient's bladder also include intermittent catheters. A typical intermittent catheter differs from an indwelling catheter primarily in that the intermittent catheter does not have a retention balloon or an associated inflation lumen. Rather, the intermittent catheter is typically a single-lumen device, with a plurality of drainage eyes at the distal end and a funnel at the proximal end. Intermittent catheterization is often performed in individuals with malfunctioning urinary systems (e.g., suffering from strictures and traumas), as well as disabled individuals (e.g., para- or quadriplegics) unable to voluntarily urinate. Such individuals will often self-catheterize with an intermittent catheter several times daily.

Intermittent catheters are generally catheters or tubes having a rounded, atraumatic distal tip that is inserted into the bladder of a patient. A molded funnel is typically connected to the proximal end that remains outside the body of the patient or user. The distal tip may include slots or openings on the shaft to facilitate drainage of urine therefrom once the tip is positioned inside the bladder.

Suitable non-limiting examples of urinary catheters, trays, insertion devices, and the like can be found in, for example, U.S. Pat. Nos. 8,328,792, 8,998,882, 10,758,705, and 10,905,848, the disclosures of which are incorporated herein by reference in their entirety.

Research suggests there is variation in all aspects of urine sampling including where the urine sample is taken from a collection system, how the urine-sampling area is cleaned, what device is used to take the urine sample, and how the urine sample is transferred to the lab. Nursing decision makers believe such variation and improper urine-sampling technique leads to an increased risk of contamination and, therefore, false-positive catheter-associated urinary tract infections ("CAUTIs"). Up to 70% of urine cultures reflect false-positive results leading to inaccurate CAUTI diagnoses and inappropriate antibiotic treatments, as well as artificially undermining the time and resources hospitals have dedicated toward reducing the risk of CAUTI by other means. This problem presents an ongoing challenge to those seeking to reduce CAUTI rates.

Disclosed herein are catheterization packages and methods thereof to facilitate catheterization and urine sampling in an effort to reduce CAUTIs and false-positive results leading to inaccurate CAUTI diagnoses.

SUMMARY

Disclosed herein is a catheterization package including, in some embodiments, catheterization-package components and a catheterization tray configured to facilitate a catheterization procedure. The catheterization-package components include a urinary catheter, a urine-drainage bag fluidly connected to the urinary catheter, and a sampling-port access device. The sampling-port access device is configured to fluidly connect to a urine-sampling port of the urinary catheter or the urine-drainage bag for aseptic collection of one or more urine samples. The catheterization tray includes a number of compartments configured to hold the catheterization-package components. A first compartment of the catheterization tray is configured to hold the urinary catheter. A second compartment of the catheterization tray is connected to the first compartment by an intercompartment connection. The second compartment is configured to hold the urine-drainage bag. A third compartment of the catheterization tray is configured to hold the sampling-port access device. Step-by-step instructions are incorporated into the catheterization tray to facilitate the catheterization procedure.

In some embodiments, the urine-drainage bag includes an inlet port and an outlet port. The outlet port includes the urine-sampling port integrated therein for the aseptic collection of the one or more urine samples with the sampling-port access device.

In some embodiments, the sampling-port access device includes a barrel, a tip at an end of the barrel, and a hollow needle coaxial with the barrel. The tip of the barrel is configured to fluidly connect the sampling-port access device to the urine-sampling port of the urinary catheter or the urine-drainage bag. The needle is fluidly connected to the tip of the barrel, but a tip of the needle is directed away from the tip of the barrel.

In some embodiments, the catheterization components further include one or more septum-stoppered test tubes configured for use with the sampling-port access device. Each test tube of the one or more test tubes has an internal pressure less than atmospheric pressure. Each test tube is independently configured to include therein a formulation for urinalysis, a formulation for microbiological analysis, or no additives or preservatives.

In some embodiments, the catheterization components further include one or more swabsticks, a package of an antiseptic skin cleanser, or a package of the one or more swabsticks in the antiseptic skin cleanser.

In some embodiments, the catheterization tray further includes an isolated fourth compartment. The fourth compartment is configured to hold the one or more swabsticks, the package of the antiseptic skin cleanser, or the package of the one or more swabsticks in the antiseptic skin cleanser.

In some embodiments, the fourth compartment includes a well and one or more channels with snap-in tabs configured to hold the one or more swabsticks respectively therein. The one or more channels are angled with respect to a top or a bottom of the catheterization tray such that one or more swab heads respectively of the one or more swabsticks are disposed in the well when snapped-in to the one or more channels.

In some embodiments, the catheterization components further include a container containing a lubricant configured for lubricating the urinary catheter in accordance with the catheterization procedure.

In some embodiments, the catheterization tray further includes a fifth compartment at least partially surrounded by the first compartment. The fifth compartment is configured to a hold the container containing the lubricant. The fifth compartment is also configured to a hold the lubricant dispensed therefrom.

In some embodiments, the catheterization components further include a specimen container configured for at least clean collection of one or more urine samples from the urine-drainage bag.

In some embodiments, the catheterization tray further includes a fifth compartment at least partially surrounded by the first compartment. The fifth compartment is configured to a hold the specimen container.

In some embodiments, the catheterization components further include a pair of examination gloves and an underpad.

In some embodiments, the catheterization package further includes packaging for the catheterization package. The packaging includes a piece of paper or paperboard, central supply room ("CSR") wrap, and an outer packaging of the catheterization package. The piece of paper or paperboard is configured to cover the catheterization tray and the catheterization components therein. The CSR wrap is configured to preserve a sterile state of the contents of the catheterization package while the CSR wrap is wrapped around the catheterization tray and the catheterization components therein. The outer packaging is configured to prevent a loss of contents of the catheterization package from a point of assembling the catheterization package to a point of using the catheterization package. The outer packaging is also configured to prevent contamination of the contents of the catheterization package from a point of ethylene-oxide sterilization of the catheterization package to the point of using the catheterization package.

Disclosed herein is a catheterization package including, in some embodiments, catheterization-package components and a molded catheterization tray configured to facilitate a catheterization procedure. The catheterization-package components include a urinary catheter, a urine-drainage bag fluidly connected to the urinary catheter, a sampling-port access device configured to fluidly connect to a urine-sampling port integrated in an outlet port of the urine-drainage bag for aseptic collection of one or more urine samples, one or more swabsticks configured for use with an antiseptic skin cleanser, and a container containing a lubricant configured for lubricating the urinary catheter. The catheterization tray includes a number of compartments configured to hold the catheterization-package components. A urinary-catheter compartment of the catheterization tray is configured to hold the urinary catheter. A urine-drainage-bag compartment of the catheterization tray is connected to the urinary-catheter compartment by an intercompartment connection. The urine-drainage-bag compartment is configured to hold the urine-drainage bag. A sampling-port-access-device compartment of the catheterization tray is configured to hold the sampling-port access device. An isolated skin-cleansing compartment is configured to hold the one or more swabsticks. A catheter-lubrication compartment is substantially surrounded by the urinary-catheter compartment. The catheter-lubrication compartment is configured to a hold the container containing the lubricant. The catheter-lubrication compartment is also configured to hold the lubricant dispensed from the container containing the lubricant. Step-by-step instructions to facilitate the catheterization procedure are embossed on the catheterization tray, printed on the catheterization tray, or embossed on the catheterization tray and printed on the catheterization tray. At least some of the step-by-step instructions for the catheterization procedure are revealed as the catheterization-package components are removed from the catheterization tray.

Also disclosed herein is a method for manufacturing a catheterization package including molding a catheterization tray configured to facilitate a catheterization procedure; incorporating step-by-step instructions into the catheterization tray for the catheterization procedure; and placing catheterization-package components in the catheterization tray. The molding includes molding a urinary-catheter compartment; molding a urine-drainage-bag compartment connected to the urinary-catheter compartment with an intercompartment connection; and molding a sampling-port-access-device compartment. Placing the catheterization-package components in the catheterization tray includes placing a urinary catheter in the urinary-catheter compartment; placing a urine-drainage bag in the urine-drainage-bag compartment; and placing a sampling-port access device in the sampling-port-access-device compartment, wherein the sampling-port access device is configured to fluidly connect to a urine-sampling port of the urinary catheter or the urine-drainage bag for aseptic collection of one or more urine samples. The urine-drainage bag is fluidly connected to the urinary catheter such that when placing the urinary catheter and the urine-drainage bag respectively in the urinary-catheter compartment and the urine-drainage-bag compartment, the urinary catheter is placed across the intercompartment connection.

In some embodiments, placing the catheterization-package components in the catheterization tray further includes placing one or more septum-stoppered test tubes configured for use with the sampling-port access device either over or under the urine-drainage bag in the urine-drainage-bag compartment.

In some embodiments, molding the catheterization tray further includes molding an isolated skin-cleansing compartment.

In some embodiments, placing the catheterization-package components in the catheterization tray further includes placing one or more swabsticks in the skin-cleansing compartment, a package of an antiseptic skin cleanser in the skin-cleansing compartment, or a package of the one or more swabsticks in the antiseptic skin cleanser in the skin-cleansing compartment.

In some embodiments, molding the catheterization tray further includes molding a catheter-lubrication compartment at least partially surrounded by the urinary-catheter compartment.

In some embodiments, placing the catheterization-package components in the catheterization tray further includes placing a container containing a lubricant in the catheter-lubrication compartment.

In some embodiments, placing the catheterization-package components in the catheterization tray further includes placing a pair of examination gloves either in or over one or more of the compartments of the catheterization tray; and folding an underpad and placing the underpad over the pair of examination gloves.

In some embodiments, the method further includes placing a piece of paper or paperboard over the catheterization tray including the catheterization components therein to form a paper- or paperboard-covered catheterization tray; wrapping CSR wrap around the paper- or paperboard-covered catheterization tray to form a CSR-wrapped catheterization tray; placing the CSR-wrapped catheterization tray in an outer packaging to form the catheterization package; and sterilizing the catheterization package by way of ethylene-oxide sterilization.

These and other features of the concepts provided herein will become more apparent to those of skill in the art in view of the accompanying drawings and following description, which disclose particular embodiments of such concepts in greater detail.

DRAWINGS

DESCRIPTION

Figure 1:
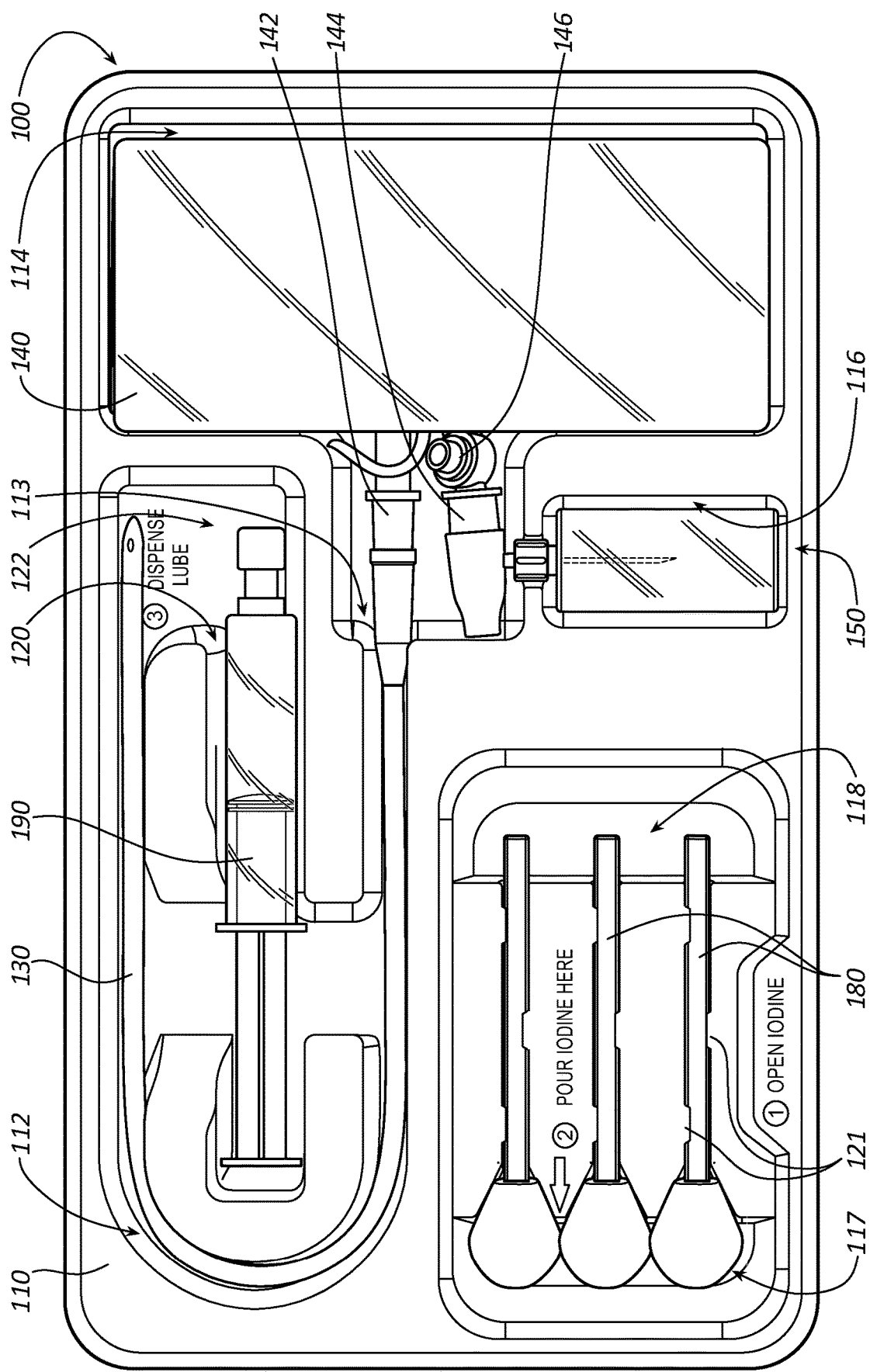
FIG. 1 illustrates at least a portion of a first catheterization package in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Disclosed herein are catheterization packages and methods thereof to facilitate catheterization and urine sampling in an effort to reduce CAUTIs and false-positive results leading to inaccurate CAUTI diagnoses.

Catheterization Packages

Figure 2:
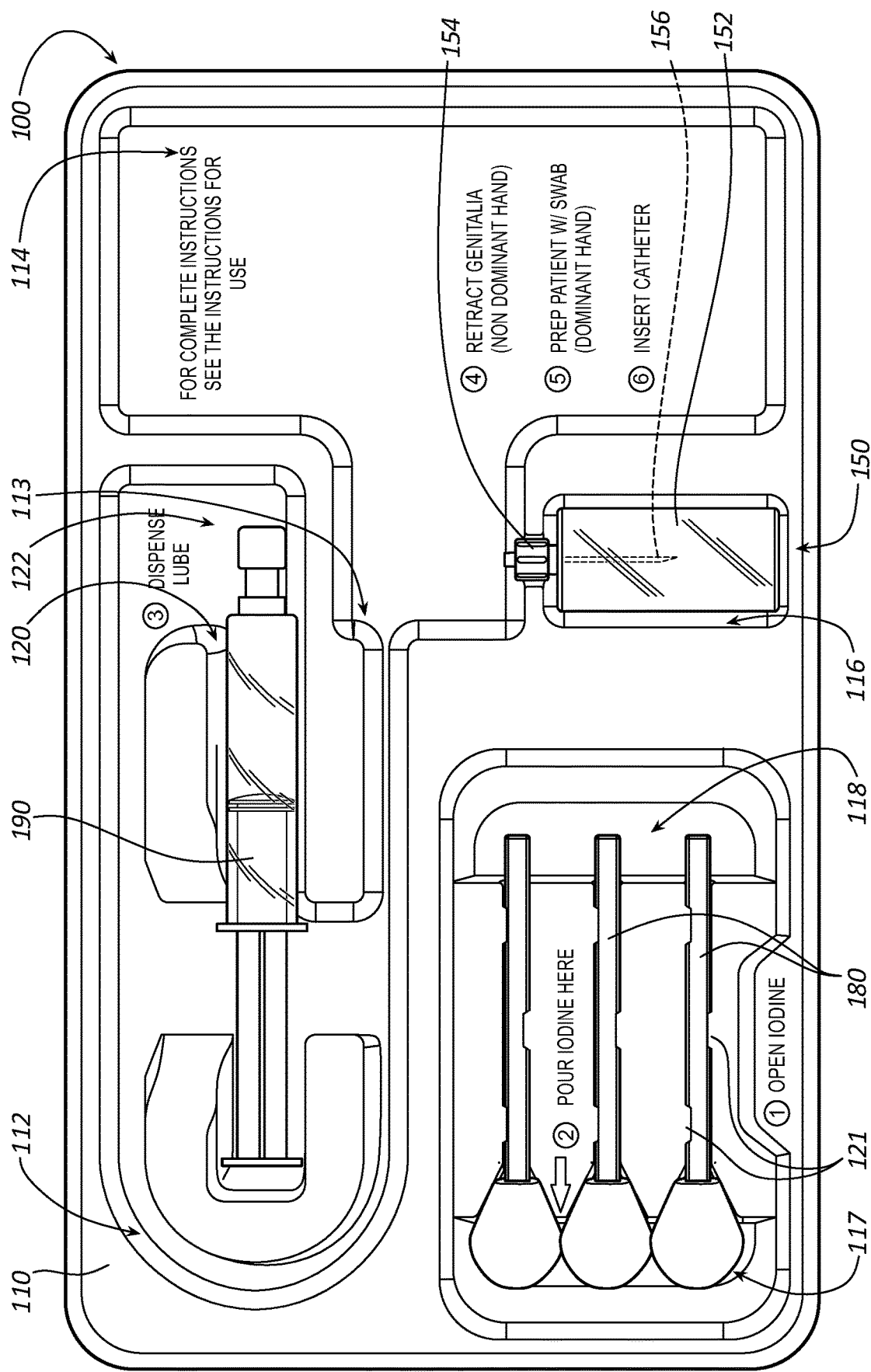
FIG. 2 illustrates some catheterization components removed from a catheterization tray of the first catheterization package in accordance with some embodiments.
Figure 3:
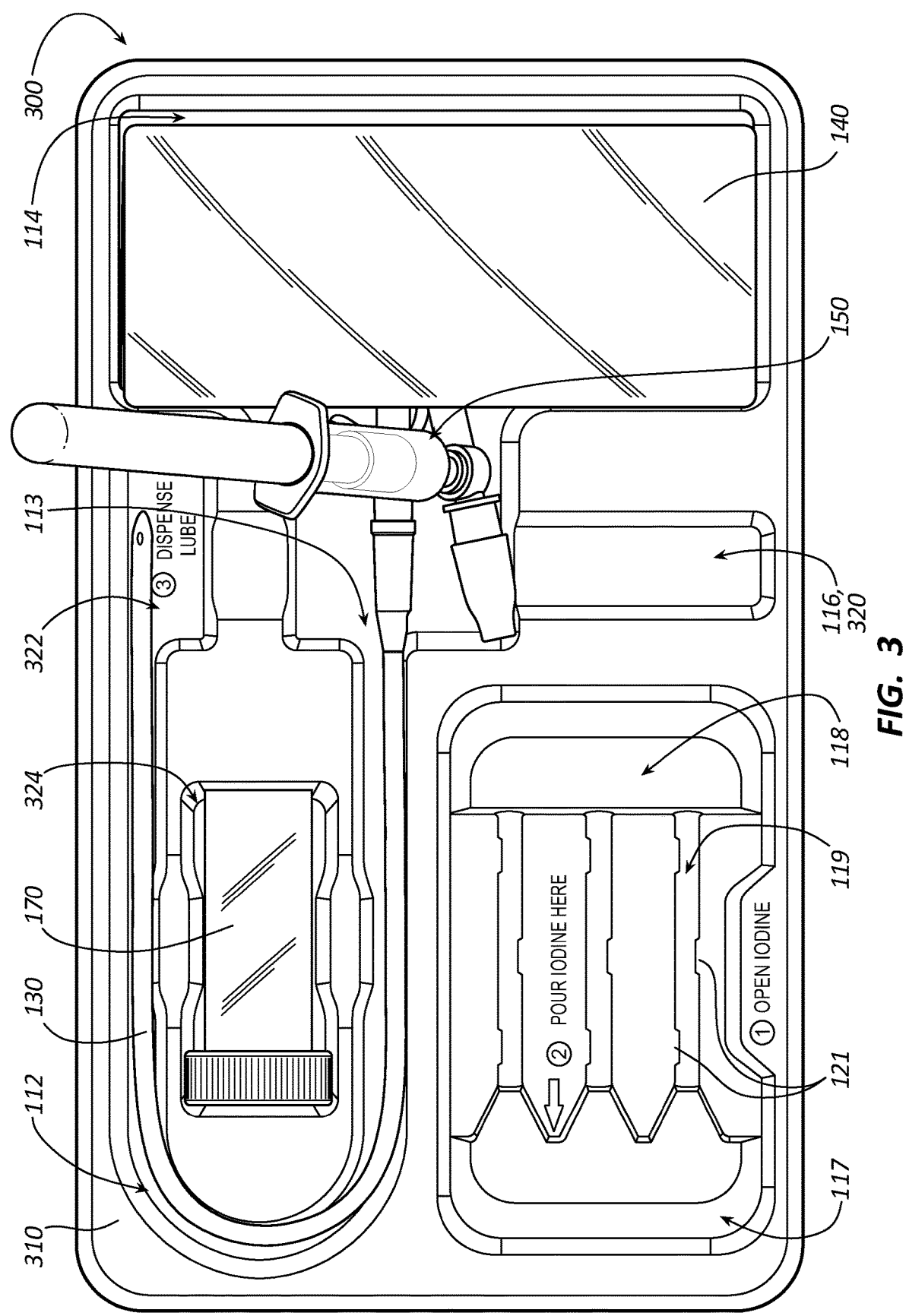
FIG. 3 illustrates at least a portion of a second catheterization package in accordance with some embodiments.
Figure 4:
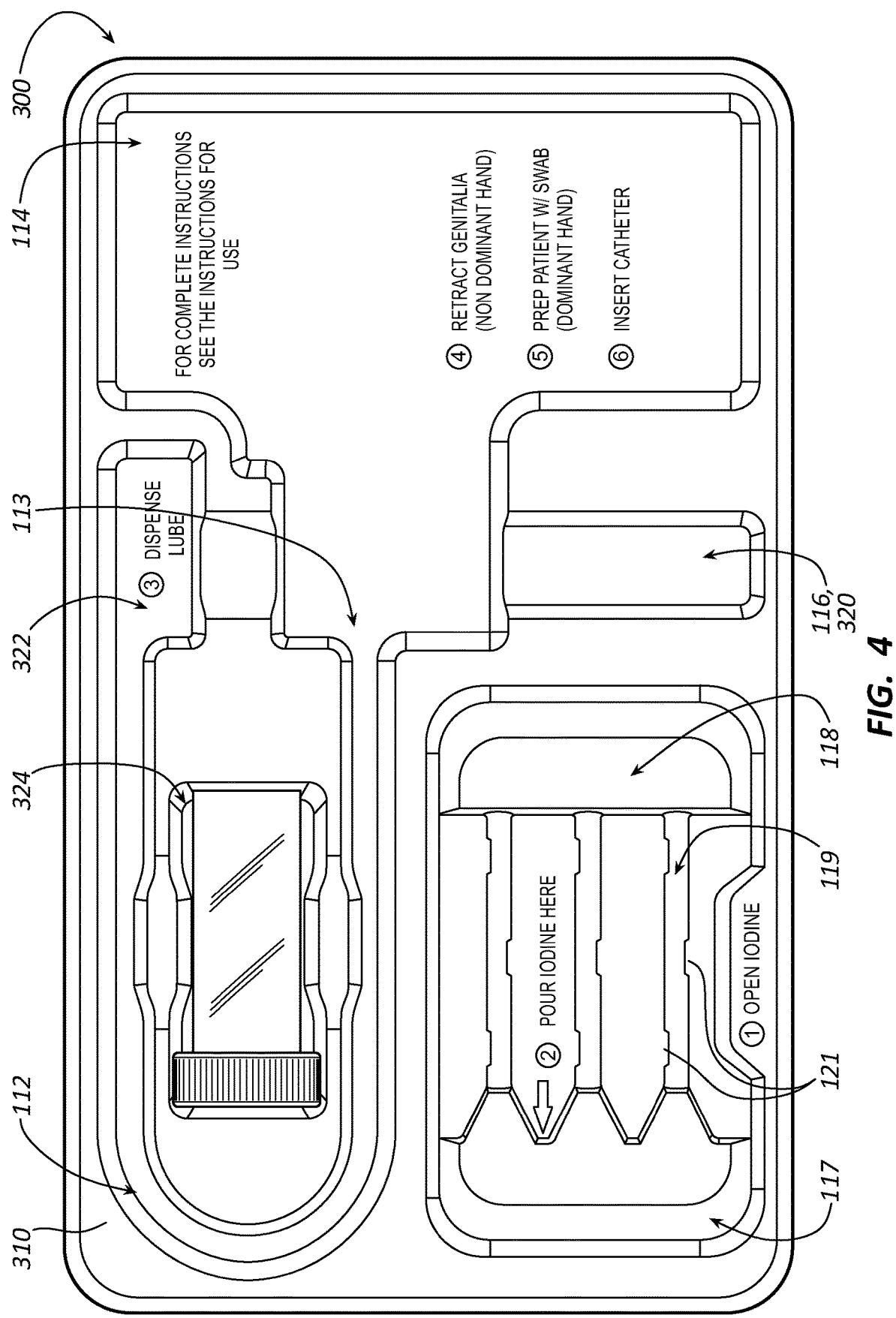
FIG. 4 illustrates some catheterization components removed from a catheterization tray of the second catheterization package in accordance with some embodiments.
Figure 6:
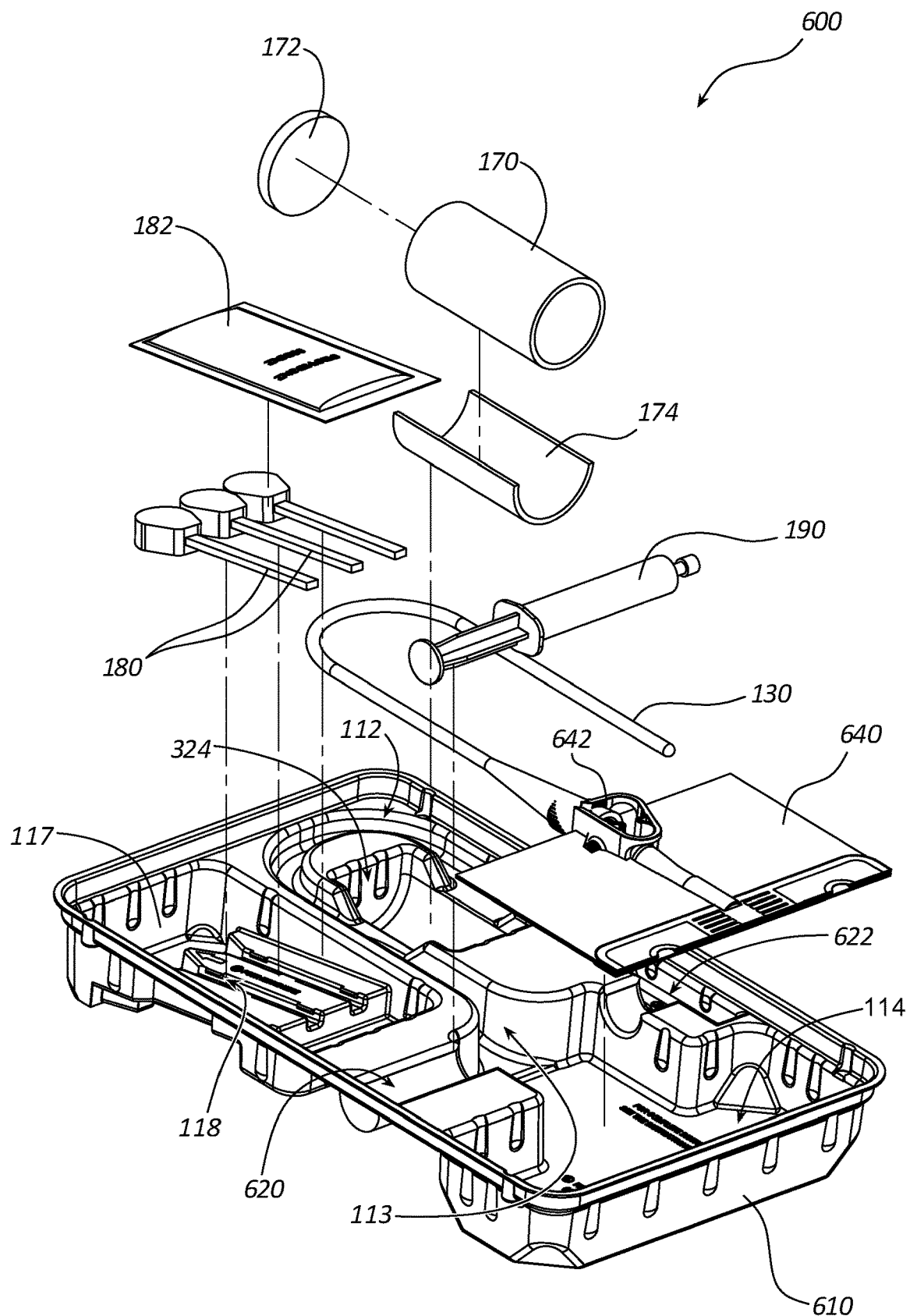
FIG. 6 illustrates an exploded view of a third catheterization package in accordance with some embodiments.
Figure 7:
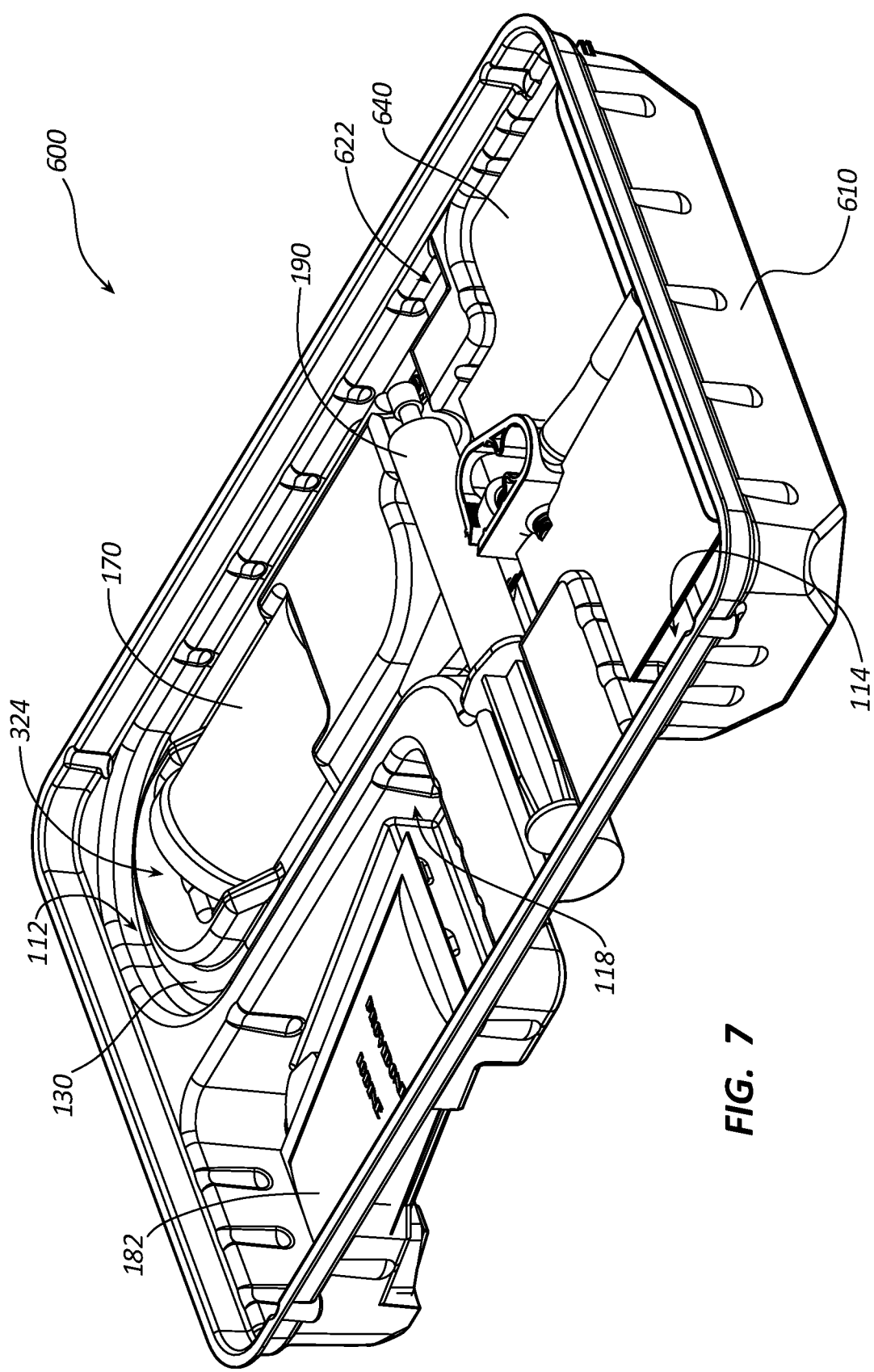
FIG. 7 illustrates at least a portion of the third catheterization package in accordance with some embodiments.
Figure 8:
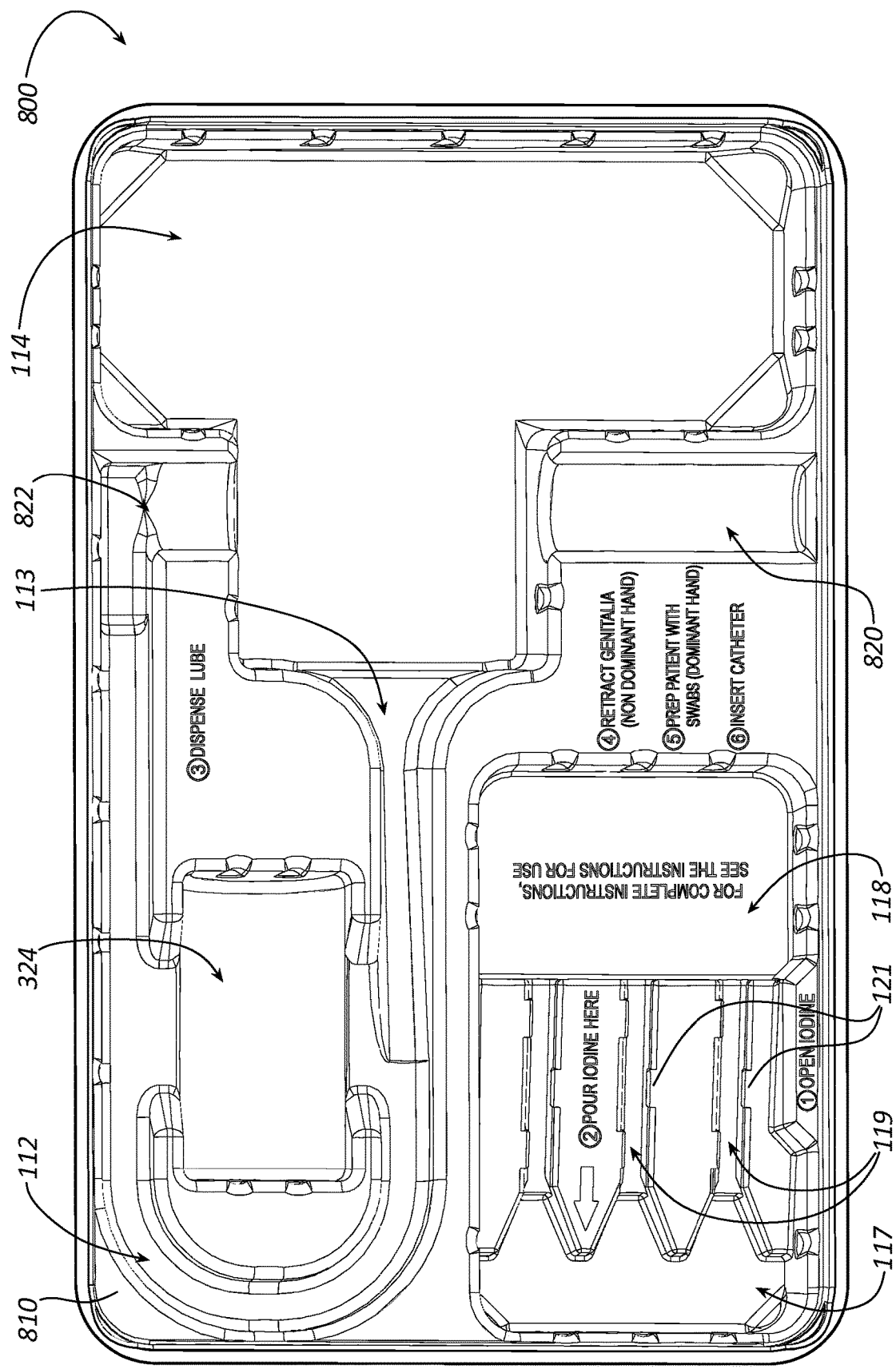
FIG. 8 illustrates at least a portion of a fourth catheterization package in accordance with some embodiments.

FIG. 1 illustrates at least a portion of a first catheterization package 100 in accordance with some embodiments. FIG. 2 illustrates some catheterization components removed from a catheterization tray 110 of the first catheterization package 100 in accordance with some embodiments. FIG. 3 illustrates at least a portion of a second catheterization package 300 in accordance with some embodiments. FIG. 4 illustrates some catheterization components removed from a catheterization tray 310 of the second catheterization package 300 in accordance with some embodiments. FIG. 6 illustrates an exploded view of a third catheterization package 600 in accordance with some embodiments. FIG. 7 illustrates at least a portion of the third catheterization package 600 in accordance with some embodiments. FIG. 8 illustrates at least a portion of a fourth catheterization package 800 in accordance with some embodiments.

As shown, the catheterization package 100, 300, 600, or 800 includes the catheterization tray 110, 310, 610, or 810 and the catheterization components set forth below, both of which are configured to facilitate a catheterization procedure. The catheterization package 100, 300, 600, or 800 is configured to facilitate the catheterization procedure by way of the catheterization components included in the catheterization package 100, 300, 600, or 800 how the catheterization components are arranged in the catheterization tray 110, 310, 610, or 810, and step-by-step instructions incorporated into the catheterization tray 110, 310, 610, or 810.

Beginning with the catheterization tray 110, 310, 610, or 810 the catheterization tray 110, 310, 610, or 810 includes a number of compartments configured to hold the catheterization components as set forth below.

A urinary-catheter compartment 112 of the catheterization tray 110, 310, 610, or 810 is configured to hold a urinary catheter.

A urine-drainage-bag compartment 114 of the catheterization tray 110, 310, 610, or 810 is connected to the urinary-catheter compartment 112 by an intercompartment connection 113. The urine-drainage-bag compartment 114 is configured to hold at least a urine-drainage bag.

A sampling-port-access-device compartment 116 of the catheterization tray 110 or 310 is configured to hold a sampling-port access device. Alternatively, the sampling-port-access-device compartment 116 of the catheterization tray 310 is a catheter-lubrication compartment 320 configured to a hold a container containing lubricant. The catheterization tray 610 or 810 includes a catheter-lubrication compartment 620 or 820 configured to a hold a container containing lubricant instead of a separate sampling-port-access-device compartment. The catheter-lubrication compartment 320, 620, or 820 is also configured to hold the lubricant dispensed from the container containing the lubricant in a well 322, 622, or 822 shared with the urinary-catheter compartment 112. Due to a lack of a sampling-port-access-device compartment in some embodiments of the catheterization tray 310, 610, or 810, the urine-drainage-bag compartment 114 doubles as the sampling-port-access-device compartment for the catheterization tray 310, 610, or 810 when a sampling-port access device is included in the catheterization packages 300, 600, and 800.

A skin-cleansing compartment 118 of the catheterization tray 110, 310, 610, or 810 is isolated from other compartments of the catheterization tray 110, 310, 610, or 810, which can be important in maintaining a sterile field about at least the urinary-catheter compartment 112. The skin-cleansing compartment 118 is configured to hold one or more swabsticks configured for skin cleansing with an antiseptic skin cleanser, a package of the antiseptic skin cleanser, or a package of the one or more swabsticks in the antiseptic skin cleanser. The skin-cleansing compartment 118 includes a well 117 and one or more channels 119 with snap-in tabs 121 configured to hold the one or more swabsticks respectively therein. The one or more channels 119 are angled with respect to a top or a bottom of the catheterization tray 110, 310, 610, or 810 such that one or more swab heads respectively of the one or more swabsticks are disposed in the well 117 when one or more stick members respectively of the one or more swabsticks are snapped-in to the one or more channels 119. The one or more stick members angle upwardly when snapped-in to the one or more channels 119 such that the one or more stick members can be grabbed and the one or more swabsticks respectively removed from the one or more channels 119. The well 117 is configured to hold the antiseptic skin cleanser therein. When the one or more swab heads are disposed in the well 117 including the antiseptic skin cleanser, the antiseptic skin cleanser saturates the one or more swab heads for antiseptic skin cleansing with the one or more swabsticks, respectively.

A catheter-lubrication compartment 120 of the catheterization tray 110 is at least partially to substantially surrounded by the urinary-catheter compartment 112. The catheter-lubrication compartment 120 is configured to a hold a container containing lubricant. The catheter-lubrication compartment 120 is also configured to hold the lubricant dispensed from the container containing the lubricant in a well 122 shared with the urinary-catheter compartment 112.

A specimen-container compartment 324 of the catheterization tray 310, 610, or 810 is also at least partially to substantially surrounded by the urinary-catheter compartment 112. The specimen-container compartment 324 is configured to a hold a specimen container. Because of the specimen-container compartment 324 in the catheterization tray 310, 610, or 810, the urinary-catheter compartment 112 doubles as the catheter-lubrication compartment for the catheterization tray 310, 610, or 810, which includes the well 322, 622, or 822 configured to hold the lubricant; however, the well 322, 622, or 822 is diminished in size compared to the well 122 of the catheterization tray 110.

The step-by-step instructions incorporated into the catheterization tray 110, 310, 610, or 810 for the catheterization procedure can be incorporated into any of the compartments of the catheterization tray 110, 310, 610, or 810, adjacent any of the compartments of the catheterization tray 110, 310, 610, or 810, or a combination thereof as best shown in FIGS. 2, 4, and 8. For example, a first step of the step-by-step instructions is directed to opening a container or package of an antiseptic skin cleanser such as a povidone-iodine solution, which first step is incorporated into the catheterization tray 110, 310, 610, or 810 adjacent the skin-cleansing compartment 118. A second step of the step-by-step instructions is directed to pouring the antiseptic skin cleanser in the well 117 of the skin-cleansing compartment 118, which second step is incorporated into the skin-cleansing compartment 118. A third step of the step-by-step instructions is directed to dispensing a lubricant in the well 122, 322, 622, or 822, which third step is incorporated into the well 122 of the catheter-lubrication compartment 120 of the catheterization tray 110, the well 322 or 622 of the urinary-catheter compartment 112 of the catheterization tray 310 or 610, or adjacent the well 822 of the urinary-catheter compartment 112 of the catheterization tray 810. A fourth step of the step-by-step instructions is directed to retracting genitalia of a patient, a fifth step of the step-by-step instructions is directed to preparing the patient with a swabstick saturated with the antiseptic skin cleanser, and a sixth step of the step-by-step instructions is directed to inserting a urinary catheter in the patient. Each step of the fourth step, the fifth step, and the sixth step of the step-by-step instructions is incorporated into the urine-drainage-bag compartment 114 of the catheterization tray 110, 310, or 610; however, due to the relatively smaller size of the urine-drainage-bag compartment 114 of the catheterization tray 810, each step of the fourth step, the fifth step, and the sixth step of the step-by-step instructions is incorporated between the skin-cleansing compartment 118 and the catheter-lubrication compartment 820 of the catheterization tray 810 for greater visibility.

As shown between FIGS. 1 and 2 or FIGS. 3 and 4, at least some of the step-by-step instructions for the catheterization procedure are revealed as the catheterization components are removed from the catheterization tray 110 or 310. While not shown, at least some of the step-by-step instructions for the catheterization procedure are also revealed as the catheterization components are removed from the catheterization tray 610 or 810. Revealing the instructions for the catheterization procedure in this way reduces procedural information to that imminently or immediately needed, which, in turn, reduces potential for informational overload, thereby simplifying the catheterization procedure.

While the catheterization trays 110, 310, 610, and 810 of FIGS. 1-4, 6, 7, and 8 are particular to some catheterization-package embodiments, other embodiments can include a different combination of compartments configured to hold a different combination of catheterization components, fewer compartments configured to hold fewer catheterization components, or more compartments configured to hold more catheterization components. For example, a catheterization tray having more compartments than the catheterization tray 310 can include all three of the sampling-port-access-device compartment 116, the catheter-lubrication compartment 320, and the specimen-container compartment 324. Such a configuration can include the catheterization tray 310 with the catheter-lubrication compartment 320 and the urine-drainage-bag compartment 114 shown in FIG. 3 but with an additional compartment (not shown) corresponding to the sampling-port-access-device compartment 116 between the catheter-lubrication compartment 320 and the urine-drainage-bag compartment 114.

The catheterization tray 110, 310, 610, or 810 can be formed by way of, for example, injection molding, whereby each of the compartments are simultaneously formed in the catheterization tray 110, 310, 610, or 810; however, the catheterization tray 110, 310, 610, or 810 is not limited to being formed by injection molding or even molding itself. If molding is used to form the catheterization tray 110, 310, 610, or 810, the step-by-step instructions can also be simultaneously formed in or on catheterization tray 110, 310, 610, or 810 as embossed step-by-step instructions. The step-by-step instructions can also be printed on the catheterization tray 110, 310, 610, or 810, either in the absence of the embossed step-by-step instructions or over the embossed step-by-step instructions to improve a contrast of the step-by-step instructions with respect to the catheterization tray 110, 310, 610, or 810.

Adverting to the catheterization components for which the catheterization tray 110, 310, 610, or 610 is configured, the catheterization components can include, but are not limited to a urinary catheter 130, a urine-drainage bag 140 or 640, a sampling-port access device 150, one or more septum-stoppered test tubes 160, a specimen container 170, one or more swabsticks 180, a container containing a lubricant 190, or a combination thereof as set forth below.

The urinary catheter 130 can be an indwelling catheter such as a Foley catheter or an intermittent catheter as shown, description for each of which is set forth above. The urinary catheter 130 is optionally already fluidly connected to the urine-drainage bag 140 or 640 in the catheterization package 100, 300, 600, or 800, which simplifies the catheterization procedure and reduces risk of inadvertently contaminating the urinary catheter 130 such as by connecting the urinary catheter 130 to the urine-drainage bag 140 or 640.

Figure 5:
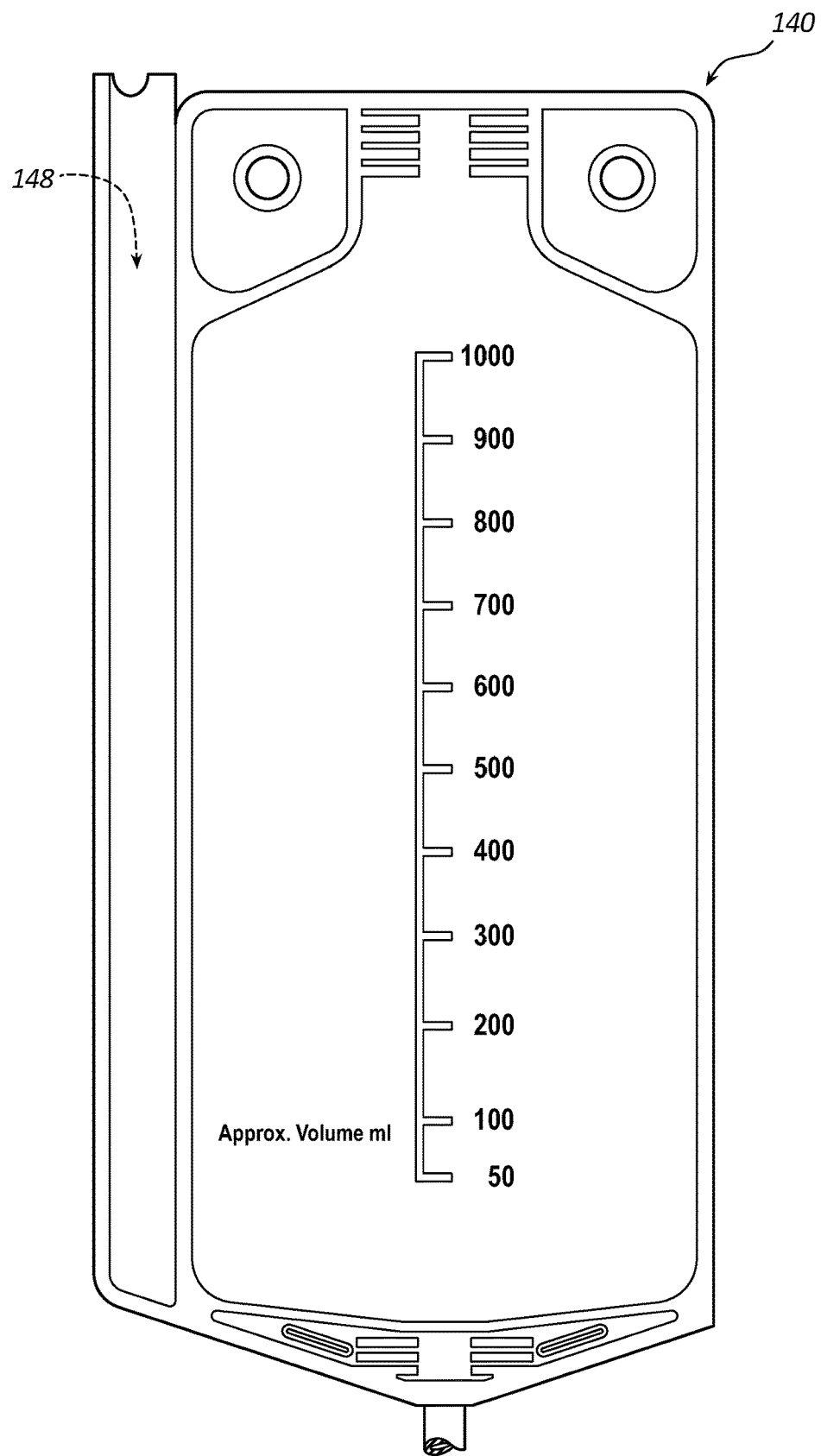
FIG. 5 illustrates at least a portion of a urine-drainage bag in accordance with some embodiments.

FIG. 5 illustrates at least a portion of the urine-drainage bag 140 in accordance with some embodiments.

The urine-drainage bag 140 includes an inlet port 142 and an outlet port 144. The outlet port 144 includes a urine-sampling port 146 integrated therein for aseptic collection of one or more urine samples with the sampling-port access device 150. As shown in FIG. 5, the urine-drainage bag 140 also includes an optional channel 148 configured to receive an intermittent catheter such as the urinary catheter 130 following use thereof for disposing the intermittent catheter with the urine-drainage bag 140.

The urine-drainage bag 640 is different than the urine-drainage bag 140 with respect to at least the arrangement of the urine-sampling port, which is integrated in the inlet port of the urine-drainage bag 640 instead of the outlet port like the urine-drainage bag 140. In addition, a tubing clamp 642 is integrated with the urine-drainage bag 640 such that the tubing clamp 642 is configured to clamp the inlet port between the urine-sampling port and a bag portion of the urine-drainage bag 640, thereby preventing any urine already present in the urine-drainage bag 640 from being sampled through the urine-sampling port. Such a configuration for the urine-drainage bag 640 ensures urine samples from the urine-sampling port are fresh from the urinary catheter 130.

The sampling-port access device 150 is configured to fluidly connect to a urine-sampling port of the urinary catheter 130 (e.g., a urine-sampling port of a Foley catheter) or the urine-sampling port 146 of the urine-drainage bag 140 for the aseptic collection of one or more urine samples. The sampling-port access device 150 includes a barrel 152, a tip 154 at an end of the barrel 152, and a hollow needle 156 coaxial with the barrel 152. The tip 154 of the barrel 152 is configured to fluidly connect the sampling-port access device 150 to the urine-sampling port of the urinary catheter or the urine-sampling port 146 of the urine-drainage bag 140. (See FIG. 3 for the sampling-port access device 150 fluidly connected to the urine-sampling port 146 of the urine-drainage bag 140.) The needle 156 is fluidly connected to the tip 154 of the barrel 152, but a tip of the needle 156 is directed away from the tip 154 of the barrel 152.

The one or more septum-stoppered test tubes 160 are configured for use with the sampling-port access device 150. Each test tube of the one or more test tubes 160 has an internal pressure less than atmospheric pressure such that urine from the urine-sampling port of the urinary catheter 130 or the urine-sampling port 146 of the urine-drainage bag 140 aspirates into the test tube when certain conditions are met. For example, urine aspirates into the test tube when the urine drainage bag 140 is at least partially filled with urine, the tip 154 of the sampling-port access device 150 is fluidly connected to the urine-sampling port 146 of the urine-drainage bag 140, and a septum stopper of the test tube is punctured by the needle 156 of the sampling-port access device 150. Each test tube is independently configured to include therein a formulation for urinalysis, a formulation for microbiological analysis, or no additives or preservatives.

The specimen container 170 is configured for at least clean collection of one or more urine samples from the urine-drainage bag 140 or 640 such as through the outlet port 144 of the urine-drainage bag 140, thereby providing an alternative to the aseptic collection of the one or more urine samples as wanted or needed. As shown in at least FIG. 6, the specimen container 170 includes a cap 172 configured to seal a urine sample in the specimen container 170. A label 174 is optionally included in the catheterization package 100, 300, 600, or 800 for labeling the specimen container 170 in accordance with any urine sample therein. The clean collection of the one or more urine samples makes use of the outlet port 144 of the urinary-drainage bag 140 and the specimen container 170 to reduce the transfer of microorganisms from health care personnel and the environment to the one or more urine samples. However, the aseptic collection of the one or more urine samples requires use of the sampling port of the urinary catheter or the sampling port 146 of the urine-drainage bag 140, the sampling-port access device 150, and the one or more test tubes 160 to not only reduce but prevent the transfer of microorganisms from health care personnel and the environment to the one or more urine samples.

The one or more swabsticks 180 are configured for skin cleansing with an antiseptic skin cleanser. The one or more swabsticks 180 are optionally already snapped-in to the one or more channels 119 of the skin-cleansing compartment 118 by the respective one or more stick members in the catheterization package 100, 300, 600, or 800. While only shown in FIGS. 6 and 7, the catheterization package 100, 300, 600, or 800 can include a package of an antiseptic skin cleanser 182, the antiseptic skin cleanser being, for example, a povidone-iodine solution for pouring in the well 117 of the skin-cleansing compartment 118 to saturate one or more swab heads respectively of the one or more swabsticks 180 for the skin cleansing. Alternatively, the one or more swabsticks 180 are packaged in the package of the antiseptic skin cleanser 182.

The container containing the lubricant 190 can be a syringe of a lubricating jelly configured to facilitate lubricating the urinary catheter 130 in the well 122 of the catheter-lubrication compartment 120 of the catheterization tray 110 or the well 322, 622, or 822 of the urinary-catheter compartment 112 of the catheterization tray 310, 610, or 810 in accordance with the catheterization procedure.

While not shown, the catheterization components for which the catheterization tray 110, 310, 610, or 810 is configured can further include, but are not limited to, one or more pairs of examination gloves and an underpad. The one or more pairs of gloves and the underpad are configured for use during the catheterization procedure such as during the skin cleansing with the antiseptic skin cleanser, lubricating the urinary catheter 130 with the lubricant in the container containing the lubricant 190, insertion of the urinary catheter 130 in the patient, or the like. The one or more pairs of gloves can be disposed in or over any of the compartments of the catheterization tray 110, 310, 610, or 810. The underpad can be folded and placed under the one or more pair of gloves, between the one or more pair of gloves, or over the one or more pairs of gloves.

While not shown, the catheterization package 100, 300, 600, or 800 further includes packaging for the catheterization package 100, 300, 600, or 800. The packaging includes a piece of paper or paperboard, CSR wrap, and an outer packaging of the catheterization package 100, 300, 600, or 800.

The piece of paper or paperboard is configured to cover the catheterization tray 110, 310, 610, or 810 and the catheterization components therein. FIGS. 1-4, 6, and 7 illustrate a lip around the catheterization tray 110, 310, 610, or 810, upon which lip the piece of paper or paperboard is configured to sit. Optionally, the piece of paper or paperboard includes product information or additional instructions to the step-by-step instructions printed thereon.

The CSR wrap is configured to preserve a sterile state of at least the catheterization components of the catheterization package 100, 300, 600, or 800 while the CSR wrap is wrapped around the catheterization tray 110, 310, 610, or 810 and the catheterization components therein.

The outer packaging is configured to prevent a loss of contents of the catheterization package 100, 300, 600, or 800 from a point of assembling the catheterization package 100, 300, 600, or 800 to a point of using the catheterization package 100, 300, 600, or 800. The outer packaging is also configured to prevent contamination of the contents of the catheterization package 100, 300, 600, or 800 from a point of ethylene-oxide sterilization of the catheterization package 100, 300, 600, or 800 to the point of using the catheterization package 100, 300, 600, or 800.

Methods

A method for manufacturing the catheterization package 100, 300, 600, or 800 includes molding the catheterization tray 110, 310, 610, or 810; incorporating the step-by-step instructions into the catheterization tray 110, 310, 610, or 810 for the catheterization procedure; and placing the catheterization components in the catheterization tray 110, 310, 610, or 810. The molding includes molding the urinary-catheter compartment 112; molding the urine-drainage-bag compartment 114 connected to the urinary-catheter compartment 112 with the intercompartment connection 113; and, for at least the catheterization tray 110 and some embodiments of the catheterization tray 310, molding the sampling-port-access-device compartment 116. Placing the catheterization components in the catheterization tray 110, 310, 610, or 810 includes placing the urinary catheter 130 in the urinary-catheter compartment 112; placing the urine-drainage bag 140 in the urine-drainage-bag compartment 114; and placing the sampling-port access device 150 in the sampling-port-access-device compartment 116 if such a compartment exists. Otherwise, the sampling-port access device 150 can be placed in the urine-drainage-bag compartment 114 as needed. The urinary catheter 130 is fluidly connected to the urine-drainage bag 140 such that when placing the urinary catheter 130 and the urine-drainage bag 140 respectively in the urinary-catheter compartment 112 and the urine-drainage-bag compartment 114, the urinary catheter 130 is placed across the intercompartment connection 113.

Placing the catheterization components in the catheterization tray 110, 310, 610, or 810 can further include placing the one or more septum-stoppered test tubes 160 for use with the sampling-port access device 150 either over or under the urine-drainage bag 140 in the urine-drainage-bag compartment 114.

Molding the catheterization tray 110, 310, 610, or 810 can further include molding the isolated skin-cleansing compartment 118.

Placing the catheterization components in the catheterization tray 110, 310, 610, or 810 can further include placing the one or more swabsticks 180 in the skin-cleansing compartment 118, a package of an antiseptic skin cleanser 182 in the skin-cleansing compartment 118, or a package of the one or more swabsticks 180 in the antiseptic skin cleanser in the skin-cleansing compartment 118.

Molding the catheterization tray 110, 310, 610, or 810 can further include molding the catheter-lubrication compartment 120 at least partially surrounded by the urinary-catheter compartment 112 or the catheter-lubrication compartment 320, 620, or 820 between the skin-cleansing compartment 118 and the urine-drainage-bag compartment 114.

Placing the catheterization components in the catheterization tray 110, 310, 610, or 810 can further include placing the container containing the lubricant 190 in the catheter-lubrication compartment 120, 320, 620, or 820.

Placing the catheterization components in the catheterization tray 110, 310, 610, or 810 can further include placing the one or more pairs of examination gloves either in or over one or more of the compartments of the catheterization tray 110, 310, 610, or 810; and folding the underpad and placing the underpad over the one or more pairs of examination gloves.

The method can further include placing a piece of paper or paperboard over the catheterization tray 110, 310, 610, or 810 including the catheterization components therein to form a paper- or paperboard-covered catheterization tray; wrapping CSR wrap around the paper- or paperboard-covered catheterization tray to form a CSR-wrapped catheterization tray; placing the CSR-wrapped catheterization tray in an outer packaging to form the catheterization package 100, 300, or 600; and sterilizing the catheterization package 100, 300, 600, or 800 by way of ethylene-oxide sterilization.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheterization package, comprising:
   catheterization-package components including:
   a urinary catheter;
   a urine-drainage bag fluidly connected to the urinary catheter; and
   a sampling-port access device configured to fluidly connect to a urine-sampling port of the urinary catheter or the urine-drainage bag for aseptic collection of one or more urine samples; and
   a catheterization tray configured to facilitate a catheterization procedure, the catheterization tray including:
   a first compartment configured to hold the urinary catheter, wherein the urinary catheter is disposed in the first compartment;
   a second compartment connected to the first compartment by an intercompartment connection, the second compartment configured to hold the urine-drainage bag, wherein the urine-drainage bag is disposed in the second compartment;
   a third compartment configured to hold the sampling-port access device, wherein the sampling-port access device is disposed in the third compartment; and
   step-by-step instructions incorporated into the catheterization tray for the catheterization procedure.

2. The catheterization package of claim 1, wherein the urine-drainage bag includes an inlet port and an outlet port, the outlet port including the urine-sampling port integrated therein for the aseptic collection of the one or more urine samples with the sampling-port access device.

3. The catheterization package of claim 1, wherein the sampling-port access device includes a barrel, a tip at an end of the barrel configured to fluidly connect the sampling-port access device to the urine-sampling port of the urinary catheter or the urine-drainage bag, and a hollow needle coaxial with the barrel, the needle fluidly connected to but directed away from the tip of the barrel.

4. The catheterization package of claim 1, the catheterization-package components further including one or more septum-stopped test tubes configured for use with the sampling-port access device, each test tube of the one or more test tubes having an internal pressure less than atmospheric pressure, wherein each test tube of the one or more test tubes is independently configured to include therein a formulation for urinalysis, a formulation for microbiological analysis, or no additives or preservatives.

5. The catheterization package of claim 1, the catheterization-package components further including one or more swabsticks, a package of an antiseptic skin cleanser, or a package of the one or more swabsticks in the antiseptic skin cleanser.

6. The catheterization package of claim 5, the catheterization tray further including an isolated fourth compartment configured to hold the one or more swabsticks, the package of the antiseptic skin cleanser, or the package of the one or more swabsticks in the antiseptic skin cleanser, wherein one of the one or more swabsticks, the package of the antiseptic skin cleanser, or the package of the one or more swabsticks in the antiseptic skin cleanser are disposed in the isolated fourth compartment.

7. The catheterization package of claim 6, wherein the fourth compartment includes a well and one or more channels with snap-in tabs configured to hold the one or more swabsticks respectively therein, and wherein the one or more channels are angled with respect to a top or a bottom of the catheterization tray such that one or more swab heads respectively of the one or more swab sticks are disposed in the well when snapped-in to the one or more channels.

8. The catheterization package of claim 1, the catheterization-package components further including a container containing a lubricant configured for lubricating the urinary catheter in accordance with the catheterization procedure.

9. The catheterization package of claim 8, the catheterization tray further including a fifth compartment at least partially surrounded by the first compartment configured to hold the container containing the lubricant, as well as the lubricant dispensed therefrom, wherein the container containing the lubricant is disposed in the fifth compartment.

10. The catheterization package of claim 1, the catheterization-package components further including a specimen container configured for at least clean collection of one or more urine samples from the urine-drainage bag.

11. The catheterization package of claim 10, the catheterization tray further including a fifth compartment at least partially surrounded by the first compartment configured to hold the specimen container, wherein the specimen container is disposed in the fifth compartment.

12. The catheterization package of claim 1, the catheterization-package components further including a pair of examination gloves and an underpad.

13. The catheterization package of claim 1, further comprising:
    packaging for the catheterization package including:
    a piece of paper or paperboard configured to cover the catheterization tray and the catheterization-package components therein;
    a central supply room ("CSR") wrap configured to preserve a sterile state of the contents of the catheterization package while the CSR wrap is wrapped around the catheterization tray and the catheterization-package components therein; and
    an outer packaging of the catheterization package, the outer packaging configured to prevent a loss of contents of the catheterization package from a point of assembling the catheterization package to a point of using the catheterization package, as well as prevent contamination of the contents of the catheterization package from a point of ethylene-oxide sterilization of the catheterization package to the point of using the catheterization package.

14. A catheterization package, comprising:
catheterization-package components including:
   a urinary catheter;
   a urine-drainage bag fluidly connected to the urinary catheter;
   a sampling-port access device configured to fluidly connect to a urine-sampling port integrated in an outlet port of the urine-drainage bag for aseptic collection of one or more urine samples;
   one or more swabsticks configured for use with an antiseptic skin cleanser;
   a container containing a lubricant configured for lubricating the urinary catheter; and
a molded catheterization tray configured to facilitate a catheterization procedure, the catheterization tray including:
   a urinary-catheter compartment configured to hold the urinary catheter, wherein the urinary catheter is disposed in the urinary-catheter compartment;
   a urine-drainage-bag compartment connected to the urinary-catheter compartment by an intercompartment connection, the urine-drainage-bag compartment configured to hold the urine-drainage bag, wherein the urine-drainage bag is disposed in the urine-drainage-bag compartment;
   a sampling-port-access-device compartment configured to hold the sampling-port access device, wherein the sampling-port access device is disposed in the sampling-port-access-device compartment;
   an isolated skin-cleansing compartment configured to hold the one or more swabsticks, wherein the one or more swabsticks are disposed in the isolated skin-cleansing compartment;
   a catheter-lubrication compartment substantially surrounded by the urinary-catheter compartment configured to a hold the container containing the lubricant, as well as the lubricant dispensed therefrom, wherein the container is disposed in the catheter-lubrication compartment; and
   step-by-step instructions for the catheterization procedure embossed on the catheterization tray, printed on the catheterization tray, or embossed on the catheterization tray and printed on the catheterization tray, at least some of the step-by-step instructions for the catheterization procedure revealed as the catheterization-package components are removed from the catheterization tray.

15. A method for manufacturing a catheterization package, comprising:
molding a catheterization tray configured to facilitate a catheterization procedure, the molding including:
   molding a urinary-catheter compartment;
   molding a urine-drainage-bag compartment connected to the urinary-catheter compartment with an intercompartment connection; and
   molding a sampling-port-access-device compartment;
incorporating step-by-step instructions into the catheterization tray for the catheterization procedure; and
placing catheterization-package components in the catheterization tray including:
   placing a urinary catheter in the urinary-catheter compartment;
   placing a urine-drainage bag in the urine-drainage-bag compartment, the urine-drainage bag fluidly connected to the urinary catheter such that the placing of the urinary catheter and the urine-drainage bag respectively in the urinary-catheter compartment and the urine-drainage-bag compartment involves placing the urinary catheter across the intercompartment connection; and
   placing a sampling-port access device in the sampling-port-access-device compartment, the sampling-port access device configured to fluidly connect to a urine-sampling port of the urinary catheter or the urine-drainage bag for aseptic collection of one or more urine samples.

16. The method of claim 15, wherein the step of placing the catheterization-package components in the catheterization tray further includes placing one or more septum-stoppered test tubes configured for use with the sampling-port access device either over or under the urine-drainage bag in the urine-drainage-bag compartment.

17. The method of claim 15, wherein the step of molding the catheterization tray further includes molding an isolated skin-cleansing compartment, and wherein placing the catheterization-package components in the catheterization tray further includes placing one or more swabsticks in the skin-cleansing compartment, a package of an antiseptic skin cleanser in the skin-cleansing compartment, or a package of the one or more swabsticks in the antiseptic skin cleanser in the skin-cleansing compartment.

18. The method of claim 15, wherein the step of molding the catheterization tray further includes molding a catheter-lubrication compartment at least partially surrounded by the urinary-catheter compartment, and wherein placing the catheterization-package components in the catheterization tray further includes placing a container containing a lubricant in the catheter-lubrication compartment.

19. The method of claim 15, wherein the step of placing the catheterization-package components in the catheterization tray further includes placing a pair of examination gloves either in or over one or more of the compartments of the catheterization tray; and folding an underpad and placing the underpad over the pair of examination gloves.

20. The method of claim 15, further comprising:
placing a piece of paper or paperboard over the catheterization tray including the catheterization-package components therein to form a paper- or paperboard-covered catheterization tray;
wrapping a central supply room ("CSR") wrap around the paper- or paperboard-covered catheterization tray to form a C SR-wrapped catheterization tray;
placing the C SR-wrapped catheterization tray in an outer packaging to form the catheterization package; and
sterilizing the catheterization package by way of ethylene-oxide sterilization.

* * * * *